United States Patent [19]

Wild

[11] Patent Number: 5,155,254
[45] Date of Patent: Oct. 13, 1992

[54] SUBSTITUTED DIONES AS INTERMEDIATES FOR A PROCESS FOR THE MANUFACTURE OF γ-PYRONES

[75] Inventor: Hans-Jakob Wild, Wolfhausen, Switzerland

[73] Assignee: Givaudan Corporation, Clifton, N.J.

[21] Appl. No.: 729,240

[22] Filed: Jul. 12, 1991

Related U.S. Application Data

[62] Division of Ser. No. 340,341, Apr. 19, 1989, Pat. No. 5,075,461.

[30] Foreign Application Priority Data

Apr. 27, 1988 [CH] Switzerland ............... 1569/88

[51] Int. Cl.$^5$ .................. C07C 65/00; C07C 65/21; C07C 69/025
[52] U.S. Cl. .................. 560/253; 560/262; 560/112; 560/110; 560/74; 560/66; 560/55; 560/20
[58] Field of Search ............ 560/253, 262, 20, 55, 560/110, 112, 66, 74

[56] References Cited

U.S. PATENT DOCUMENTS 3,832,357 8/1974 Higuchi et al. ............... 549/418

OTHER PUBLICATIONS

Cavaliere, Chem. Rev., 1947, pp. 525–584.
M. Koreeda and H. Akagi, Tetrahedron Letters 21, (1980) 1197–1200.
H. O. House, "Modern Synthetic Reactions", 2nd Edition, W. A. Benjamin, Menlo Park, CA, 1972, pp. 629–631, 734, 747–754.
R. F. Abdulla and R. S. Brinkmeyer, Tetrahedron 35, (1979) 1675, 1697–1726, 1732–1735.

*Primary Examiner*—Nicky Chan

[57] ABSTRACT

A process for the manufacture of 3-hydroxy-2-alkyl-4-pyrones of formula I is provided.

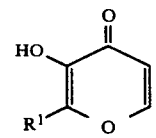

The process comprises cyclizing a compound of formula II,

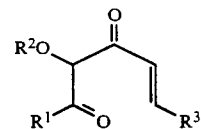

an acidic medium and hydrolyzing the ester formed thereby to produce compound I. $R^1$ represents methyl or ethyl; $R^2$ represents lower alkanoyl or optionally substituted benzoyl; $R^3$ represents —OH or —NR$^4$R$^5$; and, $R^4$ and $R^5$ may be alike or different and represent lower alkyl. The pyrones of formula I wherein $R^1$ represents methyl or ethyl are known flavorants and odorants.

5 Claims, No Drawings

SUBSTITUTED DIONES AS INTERMEDIATES FOR A PROCESS FOR THE MANUFACTURE OF γ-PYRONES

This application is a division of application Ser. No. 07/340,341, filed Apr. 19, 1989 now U.S. Pat. No. 5,075,461.

SUMMARY OF THE INVENTION

The process of this invention provides a novel method for the manufacture of γ-pyrones of formula I shown below. The γ-pyrones of formula I, wherein $R^1$ signifies methyl or ethyl, are known flavorants and odorants, and their synthesis is an object of this invention. Scheme I shows the overall process of this invention. The novel compounds of formula II are also an object of this invention.

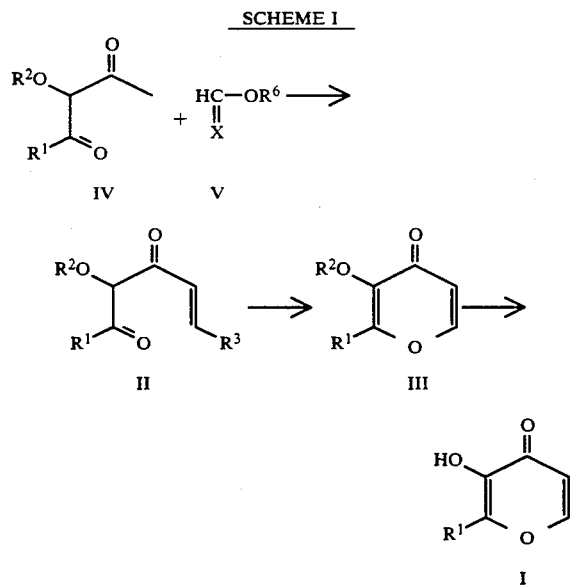

The substituents in Scheme I are identified as follows:
$R^1$ represents methyl or ethyl;
$R^2$ represents lower alkanoyl or optionally substituted benzoyl;
$R^3$ represents —OH or —$NR^4R^5$;
X represents oxygen, or the group

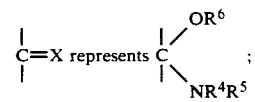

and
$R^4$, $R^5$ and $R^6$ may be alike or different and represent lower alkyl.

DESCRIPTION OF THE PREFERRED EMBODIMENTS

As shown in Scheme I, the first step of the novel synthesis, in accordance with this invention, is to prepare the compound of formula II from the compound of formula IV, by adding to it a one carbon atom unit using the formic acid derivative, V, wherein, as defined above, X is oxygen or wherein the C=X unit represents

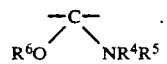

As defined previously, $R^1$ represents either methyl or ethyl.

The group $R^2$ is removed prior to the formation of the final product and its nature is not critical, any alkanoyl or optionally substituted benzoyl being suitable. The preferred alkanoyl residues are the acid residues of lower-alkanecarboxylic acids, especially of those from one to six carbon atoms Examples are acetic acid, propionic acid, butyric acid, isobutyric acid, etc. The preferred substituents on benzoyl are lower-alkyl, lower-alkoxy, halogen, nitro, alkanoyloxy, with the unsubstituted benzoyl and p-toluyl being especially preferred.

The groups $R^4$, $R^5$ and $R^6$, which can be the same or different, do not appear in the final product, so their nature is not critical. Any alkyl group would be suitable, but it is preferred to use those which contain from one to six carbon atoms. They can be straight-chain or branched. Examples are methyl, ethyl, propyl, i-propyl, butyl, hexyl. For $R^4$ and $R^5$, methyl is especially preferred. The preferred conditions of this first step depends on the nature of the substitutent X in accordance with the following Table:

| | Preparation of Compound II | | | |
|---|---|---|---|---|
| COMPOUND V | TYPE OF REACTION | REAGENT | TEMP. | LITERATURE |
| HCOR⁶ ‖ O | Claisen condensation | Strong bases e.g. alkali amides, such as lithium diisopropylamide | −78° C. to 50° C. | H. O. House, Modern Synthetic Reactions, W. A. Benjamin, Menlo Pk., Calif., 2nd ed., 1972, 629 seq. |
| HCOR⁶ / \ R⁶O  NR⁴R⁵ | Amino-methylation of IV | R⁴ \ N—CH(OR⁶)₂ / R⁵ | 20° C. to 100° C. | R. F. Abdulla, Tetrahedron 35, (1979) 1675 |

In place of IV there can, of course, also be used its enolate.

The compounds of general formula II are novel and form part of this invention.

In the next step in the process, a compound of formula II wherein $R^1$ and $R^2$ are defined previously and $R^3$ represents hydroxyl or the residue

wherein $R^4$ and $R^5$ are as previously defined, is cyclized in acidic medium, to a pyrone ring reaction product of formula III wherein $R^1$ and $R^2$ have the above significance.

The pyrone ring closure of compound II is conveniently carried out in slightly or moderately acidic medium, suitable acids being alkanecarboxylic acids, e.g. formic acid, acetic acid, propionic acid, oxalic acid, dilute mineral acids such as dilute hydrochloric acid or dilute sulphuric acid. The acid conveniently serves as the solvent. The temperature is not critical and can lie e.g. between 0° C. and 100° C.

The hydrolysis of compound III to provide I is carried out under alkaline conditions, conveniently in alkaline medium above a pH of about 10. The reaction temperature is conveniently room temperature.

One of the surprising and unexpected findings of this invention is the fact that the ring closure of compound II to III can be accomplished so readily.

The ring closure to a γ-pyrone in accordance with

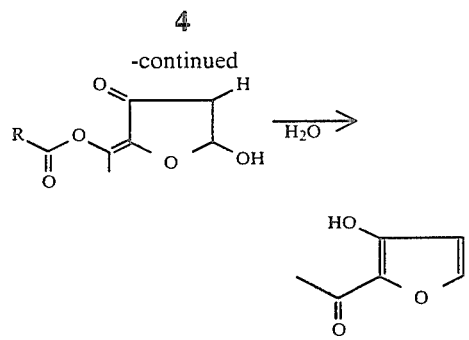

bz = benzene has been reported by M. Koreeda, Tel. Letters (1980), 1197.

In the case of compound II, because of the presence of the substituent $R^2O$, the following course leading to isomaltol would be more likely to be expected to occur:

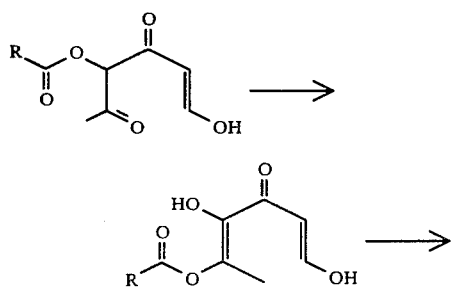

or—taking into consideration a possible hydrolysis of the ester:

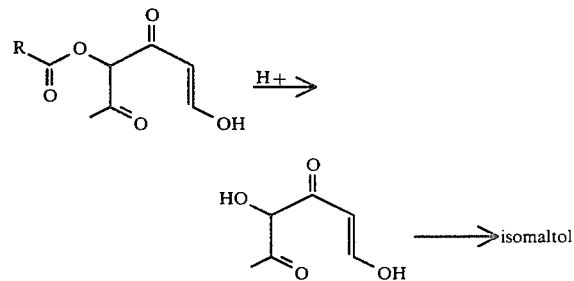

ILLUSTRATION OF THE PREFERRED EMBODIMENTS

Example 1 a) Acetylacetone (30.04 g, 300 mmol) is placed under nitrogen and treated at 0° C. within 3 hours with 40.50 g (100 mmol) of sulphuryl chloride. After the evolution of gas has finished the mixture is warmed to room temperature and stirred for 30 minutes. The reaction mixture is distilled directly at 40°–44° C./20 mbar. There are obtained 29.98 g (74%) of 3-chloro-4-hydroxy-3-penten-2-one.

IR (liq. film): 1725m, 1605s, 1400m, 1040m, 910m cm$^{-1}$.

NMR 60 MHz (CHCl$_3$): 2.3 (s,6H), 15.6 (s,1H) ppm.

MS (m/e): 134 (M$^+$), 119, 99, 92, 43 (100%).

b) Sodium benzoate (79.20 g, 550 mmol) is suspended in 1 l of N,N-dimethylformamide. Thereupon, 67.28 g (500 mmol) of 3-chloro-4-hydroxy-3-penten-2-one are allowed to flow into the suspension within 10 minutes and the mixture is stirred at 20°–25° C. for 3 hours. The reaction mixture is poured into 500 ml of 1N HCl and extracted in a separating funnel three times with 500 ml of ethyl acetate each time. The organic phases are washed with 500 ml of saturated sodium bicarbonate solution, then combined, dried over magnesium sulphate and concentrated on a rotary evaporator. The crude product distills at 106°–110° C./0.04 mbar. There are obtained 77.94 g (71%) of a tautomer mixture of 3-benzoyloxy-2,4-pentanedione + 3-benzoyloxy-4-hydroxy-3-penten-2-one in the ratio 3:1.

IR (liq. film): 3420w, 1740s (shoulder), 1720s, 1270s, 1110s, 710 cm$^{-1}$.

NMR 400 mHz (CDCl$_3$): 2.1 (s/6H), 2.4 (s/6H), 5.75 (s/1H), 7.5–8.4 (m/5H), 14.6 (s/1H) ppm.

MS (m/e): 220 (M$^+$), 178, 105 (100%), 77, 43.

c1) 3-Benzoyloxy-2,4-pentanedione (44.00 g, 200 mmol) is warmed to 40° C. 58.89 g (400 mmol) of N,N-dimethylformamide diethyl acetal are allowed to flow in within 3 hours. Subsequently, the mixture is stirred at 40° C. for a further 3 hours. The reaction mixture is concentrated on a rotary evaporator, then dissolved in 400 ml of ethyl acetate and washed in a separating funnel with 200 ml of 10% NaH$_2$PO$_4$ solution and then with 200 ml of saturated NaCl solution. The organic phase is dried over magnesium sulphate and concentrated on a rotary evaporator. The crude product is subjected to pressure-column chromatography over silica gel in ethyl acetate/hexane 4:1. There are obtained 26.37 g (48%) of 4-benzoyloxy-1-dimethylamino-1-hexene-3,5-dione.

IR (liq. film): 1730m, 1715m, 1645m, 1575s cm$^{-1}$.

NMR 60 MHz (CDCl$_3$): 2.38 (s/3H), 3.02 (d/6H), 5.38 (d/1H), 5.75 (s/1H), 7.78 (d/1H), 7.30–8.24 (m/5H) ppm.

MS (m/e): 275 (M+), 170, 105, 98 (100%), 77, 42.

d1) 4-Benzoyloxy-1-dimethylamino-1-hexene-3,5-dione (24.75 g, 90 mmol) is refluxed in 180 ml of acetic acid for 90 minutes. The reaction mixture is concentrated at 30°–35° C. on a rotary evaporator, the residue is dissolved in 200 ml of dichloromethane and washed twice with 100 ml of saturated sodium bicarbonate solution each time. The organic phase is dried over magnesium sulphate, concentrated on a rotary evaporator and gives 20.11 g (97.1%) of 3-benzoyloxy-2-methyl-4-pyrone. Content 86%, m.p. 106°–110° C.

IR (liq. film). 3000m, 1745s, 1660s cm$^{-1}$.

NMR 60 MHz (CDCl$_3$): 2.30 (s/3H), 6.48 (d/1H), 7.78 (d/1H), 7.30–8.40 (m/5H) ppm.

MS (m/e): 230 (M+), 105 (100%), 77, 43.

e1) 3-Benzoyloxy-2-methyl-4-pyrone (19.00 g, 82.6 mmol) is stirred at 20°–25° C. for 3 hours with 124 ml (248 mmol) of 2N sodium hydroxide solution. The solution is adjusted to pH 6.5 and extracted three times with 100 ml of dichloromethane each time. The combined organic phases are dried over magnesium sulphate and concentrated on a rotary evaporator. The crude product is recrystallized in acetone and gives 7.21 g (69.3%) of 3-hydroxy-2-methyl-4-pyrone, m.p. 157°–158° C.

IR (CHCl$_3$): 3420w, 3000w, 1675m, 1630s, 1570m cm$^{-1}$.

NMR 60 MHz (CDCl$_3$): 2.37 (s/3H), 6.45 (d/1H), 6.85 (s, broad/1H), 7.67 (d/1H) ppm.

MS (m/e): 126 (M+, 100%), 97, 71, 55, 43.

Example 2 c2) Diisopropylamine (48.6 g, 480 mmol) is dissolved in 350 ml of tetrahydrofuran. At −40° C. there are added dropwise thereto 275 ml (440 mmol) of 1.6 molar butyl-lithium solution in hexane. The mixture is then cooled to −78° C. and 44.02 g (200 mmol) of 3-benzoyloxy-2,4-pentane-dione in 50 ml of tetrahydrofuran are added dropwise thereto within 30 minutes. Subsequently, 22.20 g (300 mmol) of ethyl formate are added dropwise thereto at −78° C. within 30 minutes and the mixture is stirred for 2 hours. The reaction mixture is poured into 600 ml of 1N hydrochloric acid, saturated with sodium chloride and extracted three times with 500 ml of ethyl acetate each time. The combined organic phases are dried over magnesium sulphate, concentrated on a rotary evaporator and give 54.30 g of 4-benzoyloxy-1-hydroxy-1-hexene-3,5-dione.

IR (CHCl$_3$): 3000m, 1725s, 1625m cm$^{-1}$.

MS (m/e): 205, 178, 148, 122, 105 (100%), 77, 51, 43.

d2) 4-Benzoyloxy-1-hydroxy-1-hexene-3,5-dione (54.20 g, 218 mmol) is refluxed for 2 hours in 400 ml of acetic acid, the reaction mixture is concentrated at 40° C. on a rotary evaporator, the residue is dissolved in 500 ml of dichloromethane and washed twice with 300 ml of saturated sodium bicarbonate solution. The organic phase is dried over magnesium sulphate, concentrated on a rotary evaporator and gives 40.75 g (81.2%) of 3-benzoyloxy-2-methyl-4-pyrone, content 73%, m.p.: 106°–110° C.

IR (CHCl$_3$): 3000m, 1740s, 1660s cm$^{-1}$.

NMR 60 mHz (CDCl$_3$): 2.30 (s/3H), 6.48 (d/1H), 7.78 (d/1H), 7.30–8.40 (m/5H) ppm.

MS (m/e): 230 (M+), 105 (100%), 77, 43.

e2) 3-Benzoyloxy-2-methyl-4-pyrone (40.60 g, 176.5 mmol) is stirred at 20°–25° C. for 3 hours with 265 ml (530 mmol) of 2N sodium hydroxide solution. The solution is adjusted to pH 6.5 and extracted three times with 200 ml of dichloromethane each time. The combined organic phases are dried over sodium sulphate and concentrated on a rotary evaporator. The crude product is recrystallized in acetone and gives 8.90 g (40%) of 3-hydroxy-2-methyl-4-pyrone, m.p. 156°–158° C.

IR (CHCl$_3$): 3420w, 3000w, 1670m, 1630s, 1570m cm$^{-1}$.

NMR 60 mHz (CDCl$_3$): 2.37 (s/3H), 6.45 (d/1H), 6.75 (s, broad/1H), 7.67 (d/1H) ppm.

MS (m/e): 126 (M+, 100%) 97, 71, 55, 43.

I claim:

1. A compound of the formula

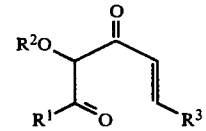

II wherein:

R$^1$ represents methyl or ethyl;

R$^2$ represents alkanoyl, benzoyl, or a substituted benzoyl having as a substituent a lower-alkyl, lower-alkoxy, halogen, nitro or an alkanoyloxy group;

R$^3$ represents

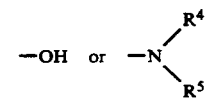

and

R$^4$ and R$^5$ are alike or different and represent lower alkyl.

2. A compound according to claim 1 wherein R$^2$ represents an alkanoyl group of from one to six carbon atoms, a benzoyl group or p-toluyl, and R$^4$ and R$^5$ represent an alkyl group of from one to six carbon atoms.

3. A compound according to claim 2 wherein R$^2$ is a benzoyl group.

4. The compound according to claim 3 known as 4-benzoyloxy-1-dimethylamino-1-hexene-3,5-dione.

5. The compound according to claim 3 known as 4-benzoyloxy-1-hydroxy-1-hexene-3,5-dione.

* * * * *